(12) United States Patent
Wariar et al.

(10) Patent No.: US 9,138,151 B2
(45) Date of Patent: *Sep. 22, 2015

(54) METHOD AND APPARATUS FOR MANAGEMENT OF HEART FAILURE HOSPITALIZATION

(71) Applicant: Cardiac Pacemakers, Inc., St. Paul, MN (US)

(72) Inventors: Ramesh Wariar, Blaine, MN (US); Jeffrey E. Stahmann, Ramsey, MN (US); Julie A. Thompson, Circle Pines, MN (US); Helen L. Reeve-Stoffer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/166,417

(22) Filed: Jan. 28, 2014

(65) Prior Publication Data

US 2014/0142440 A1    May 22, 2014

Related U.S. Application Data

(63) Continuation of application No. 13/668,659, filed on Nov. 5, 2012, now Pat. No. 8,708,924, which is a continuation of application No. 13/279,517, filed on Oct. 24, 2011, now Pat. No. 8,303,513, which is a continuation of application No. 11/685,949, filed on Mar. 14, 2007, now Pat. No. 8,052,611.

(51) Int. Cl.
*A61B 5/04*    (2006.01)
*A61B 5/0205*    (2006.01)
(Continued)

(52) U.S. Cl.
CPC .............. *A61B 5/0205* (2013.01); *A61B 5/0031* (2013.01); *A61B 5/14546* (2013.01);
(Continued)

(58) Field of Classification Search
CPC ............... A61B 5/0205; A61B 5/0031; A61B 5/14546; A61B 5/4839; A61B 5/7275; A61B 5/3431; A61B 5/0215; A61B 5/042; A61B 5/053; A61B 5/145; A61B 5/7239; A61B 7/00
USPC .................. 600/508; 607/2, 18; 128/906, 902
See application file for complete search history.

(56) References Cited

U.S. PATENT DOCUMENTS 4,562,841 A    1/1986    Brockway et al.
4,697,591 A    10/1987    Lekholm et al.
(Continued)

FOREIGN PATENT DOCUMENTS

EP    1151719 A2    11/2001
EP    1177764 A2    2/2002
(Continued)

OTHER PUBLICATIONS

"U.S. Appl. No. 11/300,675, Final Office Action mailed Aug. 5, 2009", 9 pgs.
(Continued)

*Primary Examiner* — Amanda Patton
(74) *Attorney, Agent, or Firm* — Schwegman Lundberg & Woessner, P.A.

(57) ABSTRACT

A hospitalization management system including a heart failure analyzer that receives diagnostic data including at least sensor data representative of one or more physiological signals sensed from a hospitalized patient using one or more sensors and assesses risk of rehospitalization for the patient using the diagnostic data. The outcome of the risk assessment is used during and following the patient's hospitalization for reducing the risk of rehospitalization.

20 Claims, 6 Drawing Sheets

(51) Int. Cl.

| | | |
|---|---|---|
| *A61B 5/00* | (2006.01) | |
| *G06F 19/00* | (2011.01) | |
| *A61B 5/0215* | (2006.01) | |
| *A61B 5/042* | (2006.01) | |
| *A61B 5/053* | (2006.01) | |
| *A61B 5/145* | (2006.01) | |
| *A61B 7/00* | (2006.01) | |

(52) U.S. Cl.
CPC ............ *A61B5/4839* (2013.01); *A61B 5/7275* (2013.01); *G06F 19/3431* (2013.01); A61B 5/0215 (2013.01); A61B 5/042 (2013.01); A61B 5/053 (2013.01); A61B 5/145 (2013.01); A61B 5/7239 (2013.01); A61B 7/00 (2013.01)

(56) References Cited

U.S. PATENT DOCUMENTS

| | | |
|---|---|---|
| 4,928,688 A | 5/1990 | Mower |
| 5,036,849 A | 8/1991 | Hauck et al. |
| 5,063,927 A | 11/1991 | Webb et al. |
| 5,133,353 A | 7/1992 | Hauser |
| 5,179,945 A | 1/1993 | Van Hofwegen et al. |
| 5,203,348 A | 4/1993 | Dahl et al. |
| 5,230,337 A | 7/1993 | Dahl et al. |
| 5,271,395 A | 12/1993 | Wahlstrand et al. |
| 5,284,136 A | 2/1994 | Hauck et al. |
| 5,301,677 A | 4/1994 | Hsung |
| 5,313,953 A | 5/1994 | Yomtov et al. |
| 5,314,459 A | 5/1994 | Swanson et al. |
| 5,318,597 A | 6/1994 | Hauck et al. |
| 5,334,222 A | 8/1994 | Salo et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,468,254 A | 11/1995 | Hahn et al. |
| 5,540,727 A | 7/1996 | Tockman et al. |
| 5,545,202 A | 8/1996 | Dahl et al. |
| 5,593,431 A | 1/1997 | Sheldon |
| 5,603,732 A | 2/1997 | Dahl et al. |
| 5,620,466 A | 4/1997 | Haefner et al. |
| 5,634,938 A | 6/1997 | Swanson et al. |
| 5,662,688 A | 9/1997 | Haefner et al. |
| 5,697,953 A | 12/1997 | Kroll et al. |
| 5,738,102 A | 4/1998 | Lemelson |
| 5,836,987 A | 11/1998 | Baumann et al. |
| 5,876,353 A | 3/1999 | Riff |
| 5,916,243 A | 6/1999 | KenKnight et al. |
| 5,957,861 A | 9/1999 | Combs et al. |
| 5,974,340 A | 10/1999 | Kadhiresan |
| 5,974,349 A | 10/1999 | Levine |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,073,046 A | 6/2000 | Patel et al. |
| 6,076,015 A | 6/2000 | Hartley et al. |
| 6,162,183 A | 12/2000 | Hoover |
| 6,203,495 B1 | 3/2001 | Bardy |
| 6,221,011 B1 | 4/2001 | Bardy |
| 6,261,230 B1 | 7/2001 | Bardy |
| 6,270,457 B1 | 8/2001 | Bardy |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,336,903 B1 | 1/2002 | Bardy |
| 6,358,203 B2 | 3/2002 | Bardy |
| 6,360,127 B1 | 3/2002 | Ding et al. |
| 6,368,284 B1 | 4/2002 | Bardy |
| 6,371,922 B1 | 4/2002 | Baumann et al. |
| 6,398,728 B1 | 6/2002 | Bardy |
| 6,409,675 B1 | 6/2002 | Turcott |
| 6,411,848 B2 | 6/2002 | Kramer et al. |
| 6,424,865 B1 | 7/2002 | Ding |
| 6,438,407 B1 | 8/2002 | Ousdigian et al. |
| 6,438,408 B1 | 8/2002 | Mulligan et al. |
| 6,438,410 B2 | 8/2002 | Hsu et al. |
| 6,440,066 B1 | 8/2002 | Bardy |
| 6,449,509 B1 | 9/2002 | Park |
| 6,454,719 B1 | 9/2002 | Greenhut |
| 6,459,929 B1 | 10/2002 | Hopper et al. |
| 6,473,640 B1 | 10/2002 | Erlebacher |
| 6,480,733 B1 | 11/2002 | Turcott |
| 6,513,532 B2 | 2/2003 | Mault et al. |
| 6,527,729 B1 | 3/2003 | Turcott |
| 6,542,775 B2 | 4/2003 | Ding et al. |
| 6,564,106 B2 | 5/2003 | Guck et al. |
| 6,572,557 B2 | 6/2003 | Tchou et al. |
| 6,579,242 B2 | 6/2003 | Bui et al. |
| 6,589,188 B1 | 7/2003 | Street et al. |
| 6,597,951 B2 | 7/2003 | Kramer et al. |
| 6,600,949 B1 | 7/2003 | Turcott |
| 6,607,485 B2 | 8/2003 | Bardy |
| 6,641,542 B2 | 11/2003 | Cho et al. |
| 6,645,153 B2 | 11/2003 | Kroll et al. |
| 6,650,939 B2 | 11/2003 | Taepke, II et al. |
| 6,658,292 B2 | 12/2003 | Kroll et al. |
| 6,666,826 B2 | 12/2003 | Salo et al. |
| 6,705,990 B1 | 3/2004 | Gallant et al. |
| 6,708,058 B2 | 3/2004 | Kim et al. |
| 6,738,667 B2 | 5/2004 | Deno et al. |
| 6,741,885 B1 | 5/2004 | Park et al. |
| 6,752,765 B1 | 6/2004 | Jensen et al. |
| 6,773,404 B2 | 8/2004 | Poezevera |
| 6,811,537 B2 | 11/2004 | Bardy |
| 6,827,690 B2 | 12/2004 | Bardy |
| 6,829,503 B2 | 12/2004 | Alt |
| 6,830,548 B2 | 12/2004 | Bonnet et al. |
| 6,832,113 B2 | 12/2004 | Belalcazar |
| 6,852,080 B2 | 2/2005 | Bardy |
| 6,856,829 B2 | 2/2005 | Ohsaki et al. |
| 6,860,897 B2 | 3/2005 | Bardy |
| 6,866,629 B2 | 3/2005 | Bardy |
| 6,869,404 B2 | 3/2005 | Schulhauser et al. |
| 6,887,201 B2 | 5/2005 | Bardy |
| 6,893,397 B2 | 5/2005 | Bardy |
| 6,905,463 B2 | 6/2005 | Bardy |
| 6,908,431 B2 | 6/2005 | Bardy |
| 6,908,437 B2 | 6/2005 | Bardy |
| 6,913,577 B2 | 7/2005 | Bardy |
| 6,922,587 B2 | 7/2005 | Weinberg |
| 6,945,934 B2 | 9/2005 | Bardy |
| 6,960,167 B2 | 11/2005 | Bardy |
| 6,961,615 B2 | 11/2005 | Kroll et al. |
| 6,974,413 B2 | 12/2005 | Bardy |
| 6,993,389 B2 | 1/2006 | Ding et al. |
| 7,013,176 B2 | 3/2006 | Ding et al. |
| 7,020,521 B1 | 3/2006 | Brewer et al. |
| 7,035,684 B2 | 4/2006 | Lee |
| 7,041,061 B2 | 5/2006 | Kramer et al. |
| 7,070,562 B2 | 7/2006 | Bardy |
| 7,096,064 B2 | 8/2006 | Deno et al. |
| 7,104,955 B2 | 9/2006 | Bardy |
| 7,113,823 B2 | 9/2006 | Yonce et al. |
| 7,115,096 B2 | 10/2006 | Siejko et al. |
| 7,127,290 B2 | 10/2006 | Girouard et al. |
| 7,158,830 B2 | 1/2007 | Yu et al. |
| 7,181,285 B2 | 2/2007 | Lindh et al. |
| 7,206,634 B2 | 4/2007 | Ding et al. |
| 7,228,174 B2 | 6/2007 | Burnes et al. |
| 7,306,564 B2 | 12/2007 | Nakatani et al. |
| 7,310,554 B2 | 12/2007 | Kramer et al. |
| 7,343,199 B2 | 3/2008 | Hatlestad et al. |
| 7,376,457 B2 | 5/2008 | Ross |
| 7,389,141 B2 | 6/2008 | Hall et al. |
| 7,409,244 B2 | 8/2008 | Salo et al. |

(56) References Cited

U.S. PATENT DOCUMENTS

| | | | |
|---|---|---|---|
| 7,435,221 | B1 | 10/2008 | Bharmi et al. |
| 7,468,032 | B2 | 12/2008 | Stahmann et al. |
| 7,480,528 | B2 | 1/2009 | Brockway et al. |
| 7,483,743 | B2 | 1/2009 | Mann et al. |
| 7,499,750 | B2 | 3/2009 | Haefner et al. |
| 7,572,225 | B2 | 8/2009 | Stahmann et al. |
| 7,606,617 | B2 | 10/2009 | Wariar |
| 7,662,105 | B2 | 2/2010 | Hatlestad |
| 7,680,534 | B2 | 3/2010 | Hopper |
| 7,803,118 | B2 | 9/2010 | Reisfeld et al. |
| 8,052,611 | B2 | 11/2011 | Wariar et al. |
| 8,303,513 | B2 | 11/2012 | Wariar et al. |
| 8,708,924 | B2 | 4/2014 | Wariar et al. |
| 2004/0006278 | A1 | 1/2004 | Webb et al. |
| 2004/0116819 | A1 | 6/2004 | Alt |
| 2004/0122294 | A1 | 6/2004 | Hatlestad et al. |
| 2004/0127792 | A1 | 7/2004 | Siejko et al. |
| 2004/0133079 | A1 | 7/2004 | Mazar et al. |
| 2004/0230230 | A1 | 11/2004 | Lindstrom et al. |
| 2005/0085738 | A1 | 4/2005 | Stahmann et al. |
| 2005/0137629 | A1 | 6/2005 | Dyjach et al. |
| 2005/0216067 | A1 | 9/2005 | Min et al. |
| 2005/0234355 | A1 | 10/2005 | Rowlandson |
| 2005/0256545 | A1 | 11/2005 | Koh et al. |
| 2006/0020295 | A1 | 1/2006 | Brockway et al. |
| 2006/0167516 | A1 | 7/2006 | Kjellstrom et al. |
| 2007/0055115 | A1 | 3/2007 | Kwok et al. |
| 2007/0073168 | A1 | 3/2007 | Zhang et al. |
| 2007/0083241 | A1 | 4/2007 | Bardy |
| 2007/0118183 | A1 | 5/2007 | Gelfand et al. |
| 2007/0135725 | A1 | 6/2007 | Hatlestad |
| 2007/0149862 | A1 | 6/2007 | Pipke |
| 2007/0191697 | A1 | 8/2007 | Lynn et al. |
| 2007/0208266 | A1 | 9/2007 | Hadley |
| 2007/0213621 | A1 | 9/2007 | Reisfeld et al. |
| 2008/0114219 | A1 | 5/2008 | Zhang et al. |
| 2008/0162182 | A1 | 7/2008 | Cazares et al. |
| 2008/0228090 | A1 | 9/2008 | Wariar et al. |
| 2008/0262360 | A1 | 10/2008 | Dalal et al. |
| 2008/0312541 | A1 | 12/2008 | Lewicke et al. |
| 2009/0198139 | A1 | 8/2009 | Lewicke et al. |
| 2009/0234240 | A1 | 9/2009 | Kuenzler et al. |
| 2009/0324034 | A1 | 12/2009 | Watson et al. |
| 2010/0073170 | A1 | 3/2010 | Siejko et al. |
| 2010/0191076 | A1 | 7/2010 | Lewicke et al. |
| 2010/0198097 | A1 | 8/2010 | Sowelam |
| 2011/0009760 | A1 | 1/2011 | Zhang et al. |
| 2012/0041325 | A1 | 2/2012 | Wariar et al. |
| 2013/0060151 | A1 | 3/2013 | Wariar et al. |

FOREIGN PATENT DOCUMENTS

| | | |
|---|---|---|
| JP | 119705 A | 1/1999 |
| JP | 20005145 A | 1/2000 |
| JP | 2001185238 A | 7/2001 |
| JP | 2003220039 A | 8/2003 |
| JP | 2005515043 A | 5/2005 |
| JP | 2007502670 A | 2/2007 |
| JP | 2007503286 A | 2/2007 |
| JP | 2007537777 A | 12/2007 |
| WO | WO-9602185 A1 | 2/1996 |
| WO | WO-9833553 A1 | 8/1998 |
| WO | WO-0240096 A1 | 5/2002 |
| WO | WO-03075744 A2 | 9/2003 |
| WO | WO-2004062485 A2 | 7/2004 |
| WO | WO-2005028029 A2 | 3/2005 |
| WO | WO-2008085309 A1 | 7/2008 |

OTHER PUBLICATIONS

"U.S. Appl. No. 11/300,675, Non Final Office Action mailed Jan. 24, 2008", 13 pgs.

"U.S. Appl. No. 11/300,675, Notice of Allowance mailed Oct. 6, 2009", 6 pgs.

"U.S. Appl. No. 11/300,675, Response filed Feb. 2, 2009 to Restriction Requirement mailed Dec. 31, 2008", 7 pgs.

"U.S. Appl. No. 11/300,675, Response filed Apr. 23, 2008 to Non Final Office Action mailed Jan. 24, 2008", 10 pgs.

"U.S. Appl. No. 11/300,675, Response filed Sep. 16, 2008 to Restriction Requirement mailed Aug. 25, 2008", 7 pgs.

"U.S. Appl. No. 11/300,675, Response filed Sep. 17, 2009 to Final Office Action mailed Aug. 5, 2009", 7 pgs.

"U.S. Appl. No. 11/300,675, Response filed Dec. 19, 2007 to Restriction Requirement mailed Oct. 30, 2007", 5 pgs.

"U.S. Appl. No. 11/300,675, Restriction Requirement mailed Aug. 25, 2008", 5 pgs.

"U.S. Appl. No. 11/300,675, Restriction Requirement mailed Oct. 30, 2007", 6 pgs.

"U.S. Appl. No. 11/300,675, Restriction Requirement mailed Dec. 31, 2008", 8 pgs.

"U.S. Appl. No. 12/787,789, Advisory Action mailed Dec. 30, 2013", 3 pgs.

"U.S. Appl. No. 12/787,789, Final Office Action mailed Jul. 5, 2013", 15 pgs.

"U.S. Appl. No. 12/787,789, Non Final Office Action mailed May 8, 2014", 16 pgs.

"U.S. Appl. No. 12/787,789, Non Final Office Action mailed Dec. 20, 2012", 15 pgs.

"U.S. Appl. No. 12/787,789, Response filed Apr. 18, 2013 to Non Final Office Action mailed Dec. 20, 2012", 12 pgs.

"U.S. Appl. No. 12/787,789, Response filed Oct. 22, 2012 to Restriction Requirement mailed Oct. 12, 2012", 7 pgs.

"U.S. Appl. No. 12/787,789, Response filed Nov. 26, 2013 to Final Office Action mailed Jul. 5, 2013", 12 pgs.

"U.S. Appl. No. 12/787,789, Restriction Requirement mailed Oct. 12, 2012", 7 pgs.

"Australian Application Serial No. 2009206541, Office Action mailed May 5, 2011", 3 pgs.

"Definition of window", [Online] Retrieved From Internet: <Dictionary.com>, (Apr. 12, 2009), 11 pgs.

"File History for European Application No. 09704414.3", Retrieved from the European Patent Office Electronic File System on May 27, 2011, 147 pgs.

"File History for European Application No. 10721084.1", Retrieved from the European Patent Office Electronic File System on Aug. 15, 2012, 43 pgs.

"File History for U.S. Appl. No. 12/356,289".

"International Application Serial No. PCT/US2010/036386, International Search Report mailed Nov. 3, 2010", 6 pgs.

"International Application Serial No. PCT/US2010/036386, Written Opinion mailed Nov. 3, 2010", 7 pgs.

"Japanese Application Serial No. 2010-543304, Office Action mailed May 8, 2012", 5 pgs.

"Japanese Application Serial No. 2010-543304, Office Action mailed Sep. 25, 2012", 4 pgs.

Altshule, et al., "The Effect of Position on Periodic Breathing in Chronic Cardiac Decomposition", New Eng. Journal of Med., vol. 259, No. 22, (Nov. 27, 1958), 1064-1066.

Butler, et al., "Beta-Blocker Use and Outcomes Among Hospitalized Heart Failure Patients", Journal of the American College of Cardiology, vol. 47, No. 12, (2006), 2462-2469.

Dark, et al., "Breathing Pattern Abnormalities and Arterial Oxygen Desaturation During Sleep in the Congestive Heart Failure Syndrome".

Dimopolou, I., et al., "Pattern of Breathing during Progressive Exercise in Chronic Heart Failure", (2001), 117-121.

Duguet, et al., "Expiratory Flow Limitation as a Determinant of Orthopnea in Acute Left Heart Failure", Journal of the American College of Cardiology, vol. 35, No. 3,, (2000), 690-700.

Hoffman, et al., "Cheyne-Stokes Respiration in Patients Recovering from Acute Cardiogenic Pulmonary Edema", (1990).

Junyu, et al., "Posture Detection Algorithm Using Multi Axis DC-Accelerometer", Pace vol. 22, (1999).

Lee, et al., "Predicting Mortality Among Patients Hospitalized for Heart Failure", derivation and validation of a clinical model, (2003), 2581-2587.

(56) References Cited

OTHER PUBLICATIONS

Rame, J. E. et al., "Outcomes after emergency department discharge with a primary diagnosis of heart failure", American Heart Journal, vol. 142(4), (Oct. 2001), 714-719.

Rees, et al., "Paroxysmal Nocturnal Dyspnoea and Periodic Respiration", (1979), 1315-1317.

Solin, et al., "Effects of Cardiac Dysfunction on Non-Hypercapnic Central Sleep Apnea", Department of Respiratory Medicine, Alfred Hospital, and Department of Medicine, Monash University Medical School, Melbourne, Victoria, Australia, (Apr. 10, 1997), 104-110.

Tkacova, et al., "Left Ventricular Volume in Patients with Heart Failure and Cheyne-Strokes Respiration during Sleep", Am Journal, Respir. Crit. Care Med., vol. 156, (1997), 1549-1555.

"U.S. Appl. No. 11/685,949, Response to Restriction Requirement filed Apr. 8, 2010", 10 pgs.

"U.S. Appl. No. 11/685,949, Non Final Office Action mailed Jan. 25, 2011", 9 pgs.

"U.S. Appl. No. 11/685,949, Notice of Allowance mailed Jul. 8, 2011", 5 pgs.

"U.S. Appl. No. 11/685,949, Response filed May 18, 2011 to Non Final Office Action mailed Jan. 25, 2011", 13 pgs.

"U.S. Appl. No. 11/685,949, Restriction Requirement mailed Mar. 9, 2010", 5 pgs.

"U.S. Appl. No. 13/279,517, Response filed Jun. 19, 2012 to Non Final Office Action mailed Apr. 3, 2012", 9 pgs.

"U.S. Appl. No. 13/279,517, Non Final Office Action mailed Apr. 3, 2012", 4 pgs.

"U.S. Appl. No. 13/279,517, Notice of Allowance mailed Jul. 9, 2012", 7 pgs.

"U.S. Appl. No. 13/668,659, Response filed Nov. 21, 2013 to Non Final Office Action mailed Aug. 23, 2013", 8 pgs.

"U.S. Appl. No. 13/668,659, Non Final Office Action mailed Aug. 23, 2013", 6 pgs.

"U.S. Appl. No. 13/668,659, Notice of Allowance mailed Dec. 10, 2013", 8 pgs.

"U.S. Appl. No. 13/668,659, Response fied Feb. 6, 2013 to Restriction Requirement mailed Jan. 18, 2013", 7 pgs.

"U.S. Appl. No. 13/668,659, Restriction Requirement mailed Jan. 18, 2013", 5 pgs.

Felker, G. M., et al., "Risk stratification after hospitalization for decompensated heart failure", J Card Fail., 10(6), (Dec. 2004), 460-6.

Felker, G. M., et al., "The problem of decompensated heart failure: nomenclature, classification, and risk stratification", Am Heart J., 145(2 Suppl), (Feb. 2003), S18-25.

Heidenreich, P. A., et al., "Health status identifies heart failure outpatients at risk for hospitalization or death", J Am Coll Cardiol., 47(4), (Feb. 21, 2006), 752-6.

Jaarsma, T., et al., "Readmission of older heart failure patients", Prog Cardiovasc Nurs., 11(1), (Winter, 1996), 15-20.

METHOD AND APPARATUS FOR MANAGEMENT OF HEART FAILURE HOSPITALIZATION

CLAIM OF PRIORITY

This application is a continuation of and claims the benefit of priority under 35 U.S.C. §120 to U.S. patent application Ser. No. 13/668,659, filed on Nov. 5, 2012, now issued as U.S. Pat. No. 8,708,924, which is a continuation of and claims the benefit of priority under 35 U.S.C. §120 to U.S. patent application Ser. No. 13/279,517, filed on Oct. 24, 2011, now issued as U.S. Pat. No. 8,303,513, which is a continuation of and claims the benefit of priority under 35 U.S.C. §120 to U.S. patent application Ser. No. 11/685,949, filed on Mar. 14, 2007, now issued as U.S. Pat. No. 8,052,611, which is hereby incorporated by reference herein in its entirety.

TECHNICAL FIELD

This document relates generally to medical device systems and particularly to a system providing for management of hospitalization of heart failure patients having implantable devices.

BACKGROUND

The heart is the center of a person's circulatory system. It includes an electro-mechanical system performing two major pumping functions. The left side of the heart, including the left atrium and left ventricle, draws oxygenated blood from the lungs and pumps it to various organs of the body to provide the organs with oxygen for their metabolic needs. This pumped blood flow is called the cardiac output. The right side of the heart, including the right atrium and right ventricle, draws deoxygenated blood from the organs and pumps it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes irregular contractions of the myocardium, a condition generally known as arrhythmia. Arrhythmia reduces the heart's pumping efficiency and hence, diminishes the cardiac output. The diminished cardiac output may also be caused by heart failure where the myocardial muscle is weakened and its contractility is reduced. A heart failure patient usually suffers from both a damaged electrical conduction system and a deteriorated myocardium. In response to the reduced cardiac output, the body attempts to adapt in a number of ways that lead to various symptoms as the heart failure condition progresses. The body retains salt and water as a result of reduced urinal output. The salt and water are then accumulated in the lung and/or in peripheral tissues. The water retention may also lead to acute pulmonary edema in which fluid leaks into the air sacs of the lung, causing the patient to gasp for breath. This condition can be fatal if not treated immediately. Another symptom of a patient with heart failure is fatigue on exertion. Once diagnosed with chronic heart failure, the patients is typically managed by interventions such as diet restriction and pharmacologic and/or device therapies. Such interventions keep the patient in a clinically stable state unless punctuated by episodes of acute heart failure decompensation. Acute heart failure decompensation is characterized by fluid overload and shortness of breath, and requires immediate treatment in a hospital or an outpatient clinical setting.

Heart failure has been recognized as a significant public health concern with a huge economic impact. Patients hospitalized with decompensated heart failure reportedly have a high rate of rehospitalization within six months (more than 50% according to some studies), with a significant percentage of them rehospitalized within a month. Hospital readmission is a principal factor responsible for the cost associated with managing heart failure. Premature hospital discharge and insufficient resolution of heart failure worsening are among the factors contributing to the high rate of rehospitalization. Therefore, there is a need to improve management of heart failure hospitalization for reducing the rate of rehospitalization.

SUMMARY

A hospitalization management system including a heart failure analyzer that receives diagnostic data including at least sensor data representative of one or more physiological signals sensed from a hospitalized patient using one or more sensors and assesses risk of rehospitalization for the patient using the diagnostic data. The outcome of the risk assessment is used during and following the patient's hospitalization for reducing the risk of rehospitalization.

In one embodiment, a hospitalization management system includes one or more sensors, a sensor processing circuit, and a heart failure analyzer. The one or more sensors sense one or more physiological signals. The sensor processing circuit produces sensor data representative of the sensed one or more physiological signals. The heart failure analyzer includes a data input, a diagnostic data processor, a mode switch, and a risk analyzer. The data input receives diagnostic data indicative of one or more conditions associated with heart failure. The data input includes a sensor data input to receive the sensor data. The diagnostic data processor produces one or more parameters using the diagnostic data. The mode switch switches an operational mode of the heart failure analyzer to a hospitalization mode in response to a mode-change command. The risk analyzer produces a risk class parameter during the hospitalization mode. The risk class parameter classifies a level of risk for rehospitalization within a specified period using the one or more parameters.

In one embodiment, a method for operating a heart failure analyzer for managing hospitalization of a heart failure patient is provided. One or more physiological signals are sensed. Sensor data representative of the sensed one or more physiological signals are produced. Diagnostic data indicative of one or more conditions associated with heart failure, including the sensor data, are received. One or more parameters are produced using the diagnostic data. An operational mode of the heart failure analyzer is switched to a hospitalization mode in response to a mode-change command. A risk class parameter is produced using the one or more parameters during the hospitalization mode. The risk class parameter classifies a level of risk for rehospitalization.

This Summary is an overview of some of the teachings of the present application and not intended to be an exclusive or exhaustive therapy of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
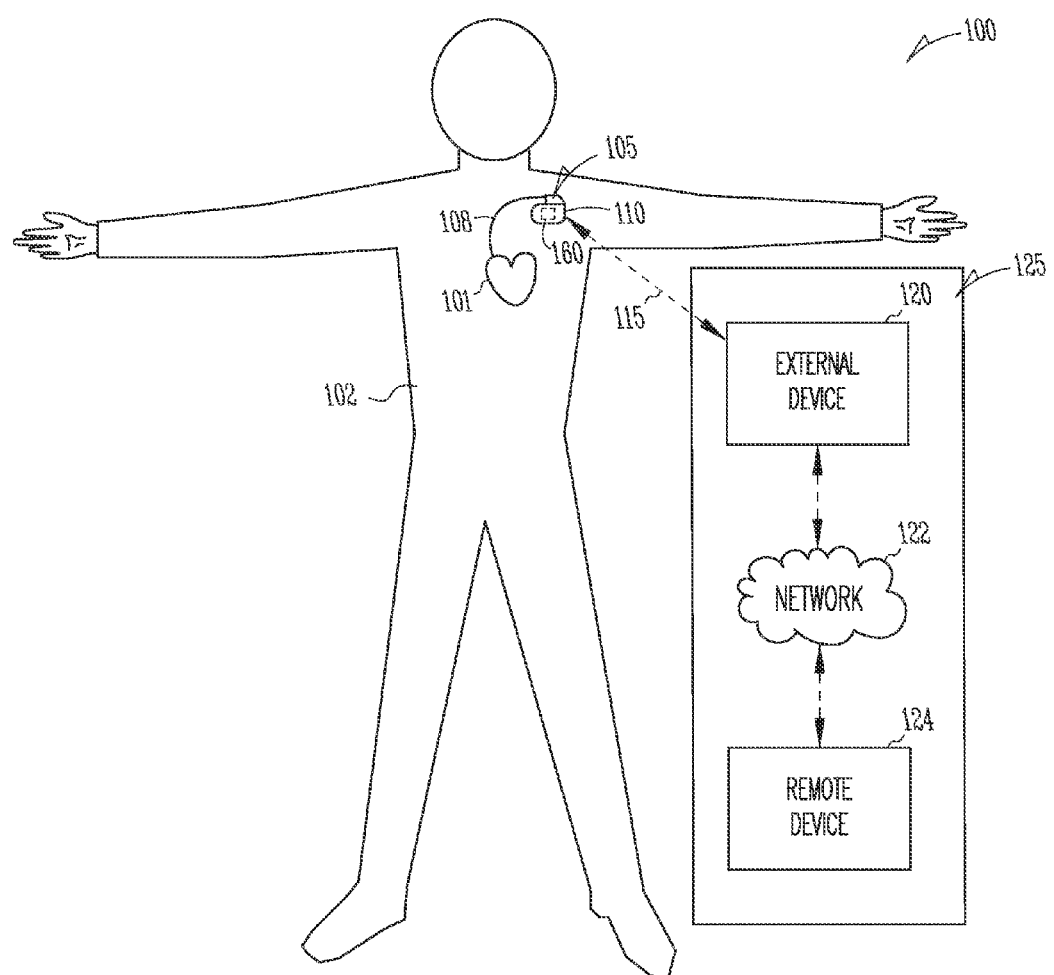
FIG. 1 is an illustration of an embodiment of a hospitalization management system and portions of the environment in which the hospitalization management system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

This document discusses a hospitalization management system that provides for management of heart failure patient including risk stratification using data acquired by a medical device implanted in the patient. Efforts have been to reduce the rate of hospitalization by, for example, assessing the risk of rehospitalization for a hospitalized patient by analyzing the patient's medical history and measurements made during hospitalization. Hospital discharge is planned based on the outcome of the risk assessment. Following the discharge, the patient is monitored for need of medical attention when certain symptoms occur. The present system automates such practice to allow them to be performed in a timely and consistent manner while the heart failure patient is in the hospital and following the patient's discharge from the hospital, thereby reducing the risk of rehospitalization and improving the patient's quality of life. In various embodiments, the present system analyzes physiological data acquired using one or more sensors implanted in the patient for therapy monitoring, risk stratification, and discharge planning during the hospitalization and for monitoring and intervention after the hospitalization. In one embodiment, the one or more sensors are part of an implantable CRM system implanted in the patient. The implantable CRM system communicates with an external patient management system that allows a physician or other caregiver to monitor, treat, and give instruction to the patient from a remote location.

In this document, "hospitalization" includes in-patient hospitalization and out-patient and clinical care. "Heart failure hospitalization" includes any hospital or clinical setting providing professional care for a heart failure patient, particularly when acute heart failure decompensation occurs.

FIG. 1 is an illustration of an embodiment of a hospitalization management system 100 and portions of the environment in which hospitalization management system 100 is used. Hospitalization management system 100 includes an implantable system 105, an external system 125, and a telemetry link 115 providing for bidirectional communication between implantable system 105 and external system 125. Implantable system 105 includes an implantable medical device 110 and a lead system 108. Implantable medical device 110 is implanted within a body 102 and coupled to a heart 101 via lead system 108. Examples of implantable medical device 110 include, but are not limited to, pacemakers, pacemaker/defibrillators, cardiac resynchronization therapy (CRT) devices, cardiac remodeling control therapy (RCT) devices, and cardiac monitors. In one embodiment, lead system 108 includes multiple atrial and ventricular leads each including one or more electrodes for pacing and/or cardioversion/defibrillation. In one embodiment, external system 125 includes a programmer. In another embodiment, as illustrated in FIG. 1, external system 125 is a patient management system including an external device 120 in proximity of implantable medical device 110, a remote device 124 in a location relatively distant from implantable medical device, and a telecommunication network 122 linking external device 120 and remote device 124. The patient management system allows access to implantable system 105 from a remote location, for purposes such as monitoring patient status and adjusting therapies. In one embodiment, telemetry link 115 is an inductive telemetry link. In another embodiment, telemetry link 115 is a far-field radio-frequency (RF) telemetry link. Telemetry link 115 provides for data transmission from implantable medical device 110 to external system 125. This may include, for example, transmitting real-time physiological data acquired by implantable medical device 110, extracting physiological data acquired by and stored in implantable medical device 110, extracting patient history data such as data indicative of occurrences of arrhythmias, occurrences of decompensation, and therapy deliveries recorded in implantable medical device 110, and extracting data indicating an operational status of implantable medical device 110 (e.g., battery status and lead impedance). Telemetry link 115 also provides for data transmission from external system 125 to implantable medical device 110. This may include, for example, programming implantable medical device 110 to acquire physiological data, programming implantable medical device 110 to perform at least one self diagnostic test (such as for a device operational status), programming implantable medical device 110 to deliver at least one therapy, and instructing implantable medical device 110 to analyzing data associated with heart failure.

Hospitalization management system 100 includes a heart failure analyzer 160 providing for hospitalization management of a heart failure patient using at least diagnostic data acquired by implantable system 105. Heart failure analyzer 160 analyzes the diagnostic data for therapy monitoring, risk stratification, and discharge planning during hospitalization of a heart failure patient and for monitoring and intervention after the hospitalization of the patient. In the illustrated embodiment, heart failure analyzer 160 is substantially included in implantable medical device 110. In another embodiment, heart failure analyzer 160 is substantially included in external system 125. In various embodiments, heart failure analyzer 160 is distributed in both implantable system 105 and external system 125. Heart failure analyzer 160 may be implemented using a combination of hardware and software. In various embodiments, each element of heart failure analyzer 160, including its specific embodiments, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof and a programmable logic circuit or a portion thereof. For example, a "timer" includes, among other things, an electronic circuit timer constructed to perform the only function of tracking time or a portion of a general-purpose circuit driven by a code instructing that portion of the general-purpose circuit to track time.

Figure 2:
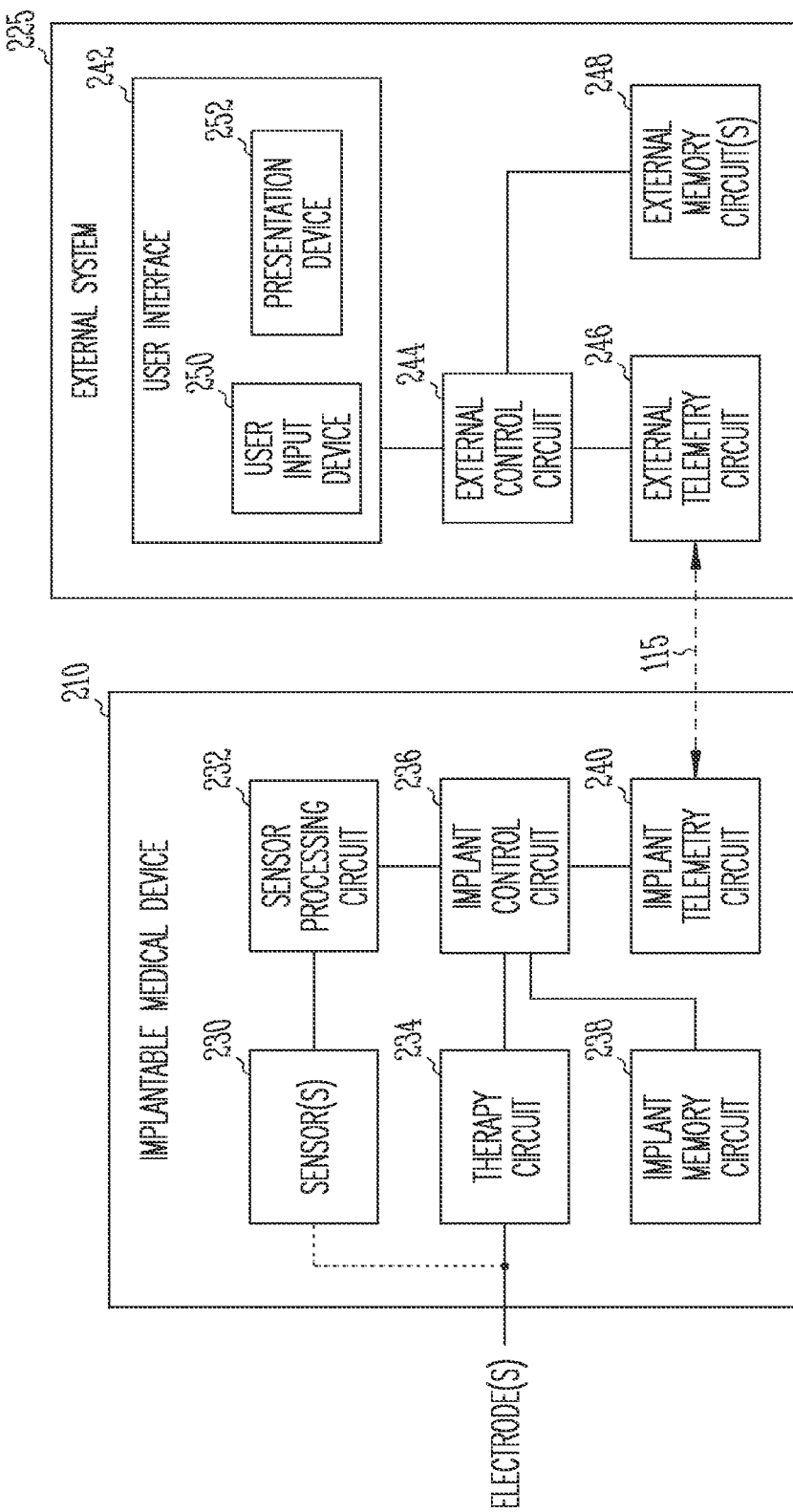
FIG. 2 is a block diagram illustrating an embodiment of portions of a circuit of the hospitalization management system.

FIG. 2 is a block diagram illustrating an embodiment of portions of a circuit of hospitalization management system 100, which includes an implantable medical device 210 and external system 225. Implantable medical device 210 represents an embodiment of implantable medical device 110 and includes one or more sensors 230, a sensor processing circuit 232, a therapy circuit 234, an implant control circuit 236, an implant memory circuit 238, and an implant telemetry circuit 240. Sensor(s) 230 sense one or more physiological signals. Examples of sensor(s) 230 include a sensing circuit that senses one or more electrograms, a heart sound sensor (such as an accelerometer or a microphone) that senses a heart sound signal, an impedance sensor that senses a transthoracic impedance, a pressure sensor that senses a blood pressure, such as a pulmonary artery pressure (PAP) sensor that senses a PAP, and a chemical sensor that senses, for example, a blood potassium level. Sensor processing circuit 232 produces sensor data representative of the sensed one or more physiological signals. Implant memory circuit 238 includes a circular buffer that stores the sensor data. Therapy circuit 234 delivers one or more therapies to body 102. In one embodiment, therapy 234 delivers one or more of an anti-bradycardia pacing therapy, an anti-tachycardia pacing therapy, a defibrillation therapy, a cardiac resynchronization therapy, and a neurostimulation therapy. In various embodiments, therapy circuit 234 includes one or more of a pacing circuit to deliver pacing pulses, a defibrillation circuit to deliver cardioversion/defibrillation pulses, a neurostimulation circuit to deliver neurostimulation, a drug delivery device to deliver one or more drugs, and a biologic therapy device to deliver one or more biologic therapies such as cell therapies and gene therapies. Implant control circuit 236 controls the operation of implantable medical device 210. Implant telemetry circuit 240 receives data from, and transmits data to, external system 225 via telemetry link 115. In one embodiment, implantable medical device 210 includes a hermetically sealed housing containing at least sensor processing circuit 232, therapy circuit 234, implant control circuit 236, implant memory circuit 238, and implant telemetry circuit 240. In various embodiments, sensor(s) 230 are each within the hermetically sealed housing or external to the hermetically sealed housing but communicatively coupled to sensor processing circuit 232 via a wired or wireless communication link.

External system 225 represents an embodiment of external system 125 and includes a user interface 242, an external control circuit 244, an external telemetry circuit 246, and one or more external memory circuits 248. These components are each included in one or both of external device 120 and remote device 124. User interface 242 allows a user such as a physician or other caregiver to control hospitalization management system 100 and include a user input device 250 and a presentation device 252. User input device 250 receives commands and parameters from the user. Presentation device 252 includes a printer and/or a display screen to present to the user various information including information indicative of operation of hospitalization management system 100 and information acquired and/or stored in various portions of hospitalization management system 100. External control circuit 244 controls the operation of external system 225. External telemetry circuit 246 receives data from, and transmits data to, implantable medical device 210 via telemetry link 115. External memory circuit(s) 248 store data including external data representative of patient information. In one embodiment, the external data include data used in management of heart failure patients and data transmitted from one or more implantable or external medical devices (other than implantable medical device 210) as well as data received by user input device 250. Examples of such external data include therapy parameters such as drug dosage and pacing parameters, diagnostic test results such as laboratory test results and medical examination results, medical history information such as patient demographics and history of cardiac conditions including heart failure symptoms and recovery information.

In one embodiment, implant control circuit 236 includes heart failure analyzer 160. In another embodiment, external control circuit 244 includes heart failure analyzer 160. In another embodiment, implant control circuit 236 and external control circuit 244 each include portions of heart failure analyzer 160. Heart failure analyzer 160 receives a mode-change command and controls the operation of implantable medical device 210 and/or external system 225 according to an operational mode selected according to the mode-change command. In one embodiment, the operational mode is selected from a hospitalization mode, a post-hospitalization mode, and a non-hospitalization mode. These operational modes each correspond to a heart failure management algorithm applied to a patient depending on the hospitalization status of that patient.

Figure 3:
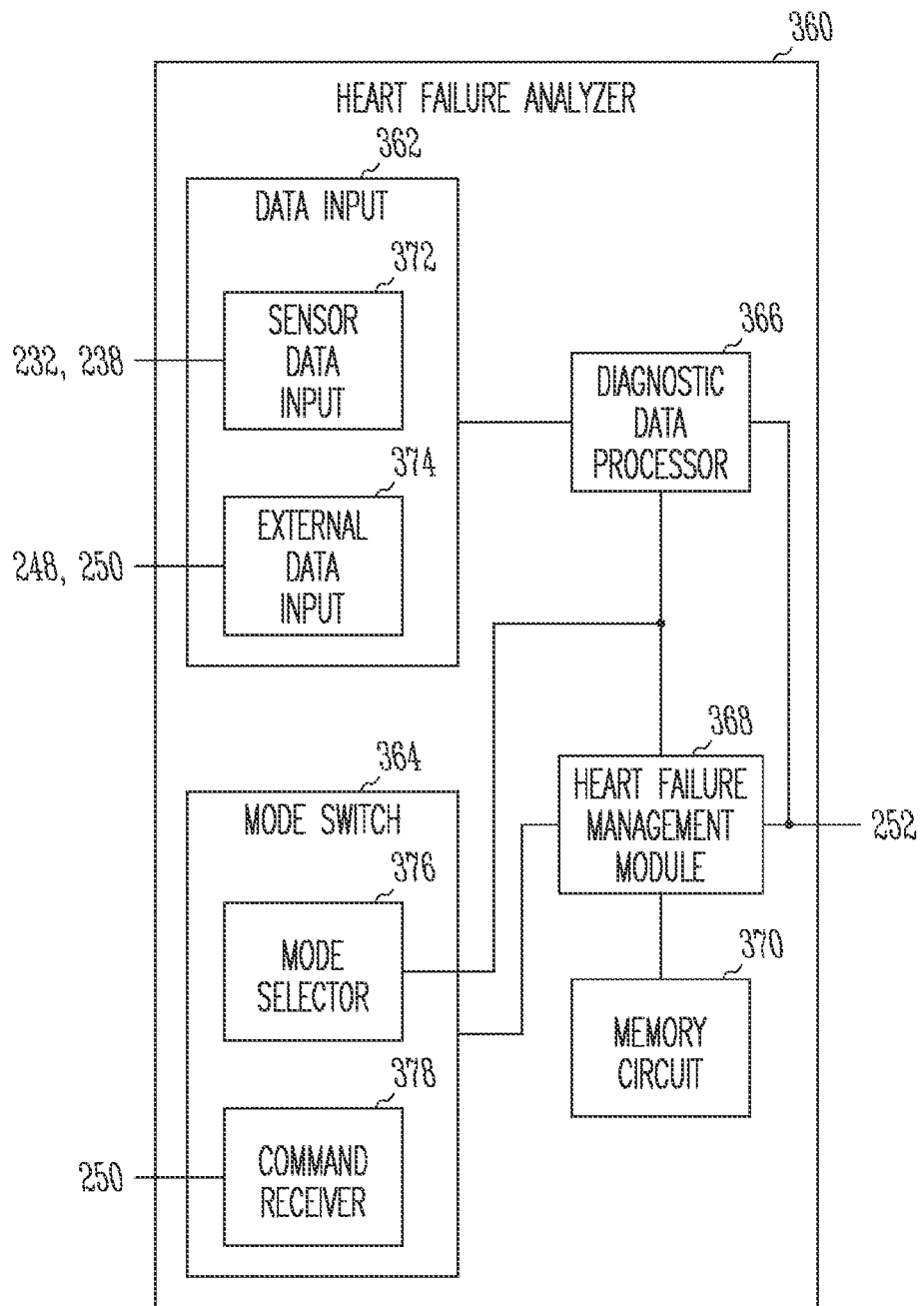
FIG. 3 is a block diagram illustrating an embodiment of a heart failure analyzer of the hospitalization management system.

FIG. 3 is a block diagram illustrating an embodiment of a heart failure analyzer 360, which represents an embodiment of heart failure analyzer 160. Heart failure analyzer 360 includes a data input 362, a mode switch 364, a diagnostic data processor 366, a heart failure management module 368, and a memory circuit 370.

Data input 362 receives diagnostic data indicative of one or more conditions associated with heart failure. In the illustrated embodiment, data input 362 includes a sensor data input 372 and an external data input 374. In other embodiments, data input 362 includes one or more of sensor data input 372 and external data input 374, depending on the need of the heart failure management algorithms executed by heart failure analyzer 360. Sensor data input 372 receives sensor data representative of one or more physiological signals sensed by sensor(s) 230 of implantable medical device 210. External data input 374 receives the external data representative of patient information from external system 225.

Figure 4:
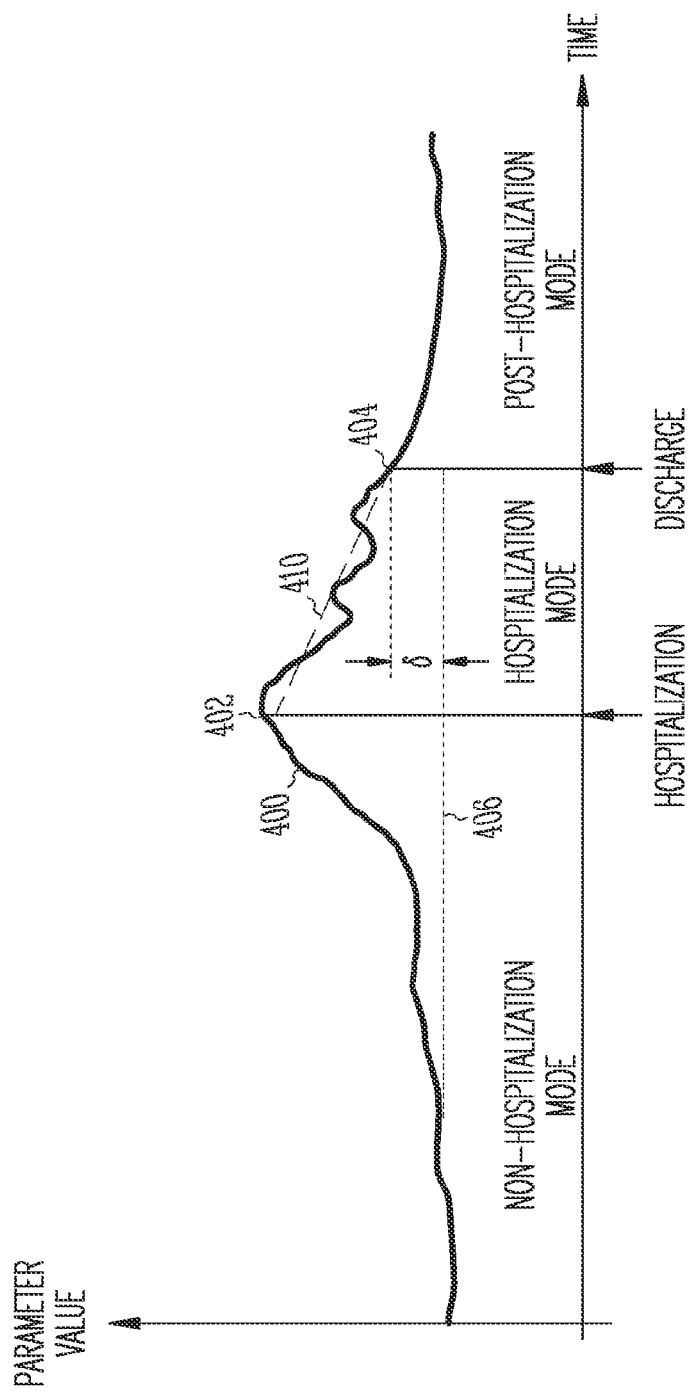
FIG. 4 is a graph illustrating an example of a parameter indicative of progression of heart failure.

Diagnostic data processor 366 produces one or more parameters indicative of one or more conditions associated with heart failure using the diagnostic data received by data input 362. Examples of such one or more parameters include amplitude of third heart sounds (S3) produced using the heart sound signal, thoracic fluid volume produced using the thoracic impedance signal, respiration rate produced using the thoracic impedance signal, heart rate and heart rate variability produced using the one or more electrograms, and parameters indicative of various physiological responses to patient's physical activities. In one embodiment, diagnostic data processor 366 produces a parameter as a function of a plurality of sensed physiological signals and patient information represented by selected sensor data and external data received by data input 362. In one embodiment, diagnostic data processor 366 produces a trend using at least one of the one or more parameters. The trend is indicative of progression of heart failure, including an acute worsening of heart failure. An example of such a trend is illustrated in FIG. 4, which is further discussed below. In one embodiment, diagnostic data processor 366 produces a trend of the parameter as the function of the plurality of sensed physiological signals and patient information. In one embodiment, the one or more parameters produced by diagnostic data processor 366, including the trend, is presented using presentation device 252.

Mode switch 364 switches the operational mode of heart failure analyzer 360 to one of a hospitalization mode, a post-hospitalization mode, and a non-hospitalization mode in response to a mode-change command. In the illustrated embodiment, mode switch 364 includes a mode selector 376 and a command receiver 378. In other embodiments, mode switch 364 includes any one or more of mode selector 376 and command receiver 378, depending on how heart failure analyzer 160 determines the hospitalization status of the patient. Mode selector 376 produces the mode-change command automatically using the one or more parameters produced by diagnostic data processor 366. Command receiver 378 receives the mode-change command from external system 225. In one embodiment, the mode-change command is entered by the user through user input device 250.

Heart failure management module 368 executes a heart failure management algorithm selected from one or more stored heart failure management algorithms according to the operational mode. Memory circuit 370 stores the one or more heart failure management algorithms, including at least a hospitalization algorithm that is to be executed while the patient is hospitalized. In one embodiment, memory circuit 370 stores a post-hospitalization algorithm in addition to the hospitalization algorithm. The post-hospitalization algorithm is to be executed during a post-hospitalization period after the discharge of the patient from the hospital. In another embodiment, memory circuit 370 stores a baseline algorithm in addition to the hospitalization algorithm and the post-hospitalization algorithm. The baseline algorithm is to be executed after the post-hospitalization period and before the patient is hospitalized.

FIG. 4 is a graph illustrating an example of a parameter 400 indicative of progression of heart failure, including the acute worsening of heart failure. Parameter 400 is for illustrative purpose only and represents the one or more parameters produced by diagnostic data processor 366. As illustrated, the amplitude of parameter 400 indicates the degree of severity of heart failure in a patient. In the illustrated embodiment, the one or more heart failure management algorithms stored in memory circuit 370 include the baseline algorithm, the hospitalization algorithm, and the post-hospitalization algorithm.

During the non-hospitalization mode, parameter 400 indicates a degree of severity of heart failure that does not require hospitalization. When parameter 400 indicates that the patient is clinically stable (without symptoms indicating a substantially degree of decompensation for 30 days, for example), heart failure management module 368 establishes a baseline value 406 for parameter 400, using the one or more parameters produced using data acquired during the clinically stable period, by executing the baseline algorithm during the non-hospitalization mode. In one embodiment, data input 362 receives data selected according to the requirement of the baseline algorithm, and diagnostic data processor 366 produces parameter 400 using the selected data. In one embodiment, selected one or more physiological signals represented by the received data are smoothed with filters such as finite impulse response, infinite impulse response, and/or nonlinear filters. In another embodiment, regression analysis or curve fitting are used to estimate baseline value 406.

At 402, mode switch 364 switches the operational mode of heart failure analyzer 360 to the hospitalization mode from the non-hospitalization mode when parameter 400 exceeds a hospitalization threshold value, or when a user command is received following the patient's admission into a hospital. During the hospitalization mode, heart failure management module 368 analyzes therapy efficacy, produces therapy adjustment signals when necessary, and assesses risk of rehospitalization using parameter 400 by executing the hospitalization algorithm. In one embodiment, the therapy efficacy is analyzed by comparing parameter 400 to its expected value 410 that is determined according to one or more therapies applied to the patient. In various embodiments, the therapy adjustment signals are presented to the physician or other caregiver and/or result in automatic adjustment of therapy delivery. In one embodiment, data input 362 receives data selected according to the requirement of the hospitalization algorithm, and diagnostic data processor 366 produces parameter 400 using the selected data.

At 404, mode switch 364 switches the operational mode of heart failure analyzer 360 to the post-hospitalization mode from the hospitalization mode when parameter 400 decreases below a discharge threshold value, or when a user command is received after a decision to discharge the patient from the hospital is made. Readiness to discharge is determined by comparing one or more features extracted from parameter 400 during the hospitalization mode to corresponding one or more criteria statistically established using a patient population. Examples of such features include change of value of parameter 400 from baseline value 406, change of value of parameter 400 from its peak value prior to the hospitalization, a derivative of parameter 400, a frequency-domain feature of parameter 400, and a measure of variance of parameter 400. In one embodiment, as illustrated in FIG. 4, the readiness to discharge is indicated when parameter 400 does not exceed baseline value 406 by a predetermined margin b. During the post-hospitalization mode, heart failure management module 368 monitors cardiac conditions and determines a need for intervention including rehospitalization using parameter 400 by executing the post-hospitalization algorithm. The need for intervention including rehospitalization is determined by comparing one or more features extracted from parameter 400 during the post-hospitalization mode to corresponding one or more criteria statistically established using the patient population. Examples of such features also include change of value of parameter 400 from baseline value 406, change of value of parameter 400 from its peak value prior to the hospitalization, a derivative of parameter 400, a frequency-domain feature of parameter 400, and a measure of variance of parameter 400. In one embodiment, the need for rehospitalization is indicated when parameter 400 exceeds baseline value 406 by a predetermined margin 6, or when a positive slope of parameter exceeds a predetermined threshold, during the post-hospitalization mode. In one embodiment, the predetermined margin or threshold for rehospitalization is lower than that of hospitalization but higher than that required to transition from the hospitalization mode to the post-hospitalization mode. In one embodiment, data input 362 receives data selected according to the requirement of the post-hospitalization algorithm, and diagnostic data processor 366 produces parameter 400 using the selected data.

Figure 5:
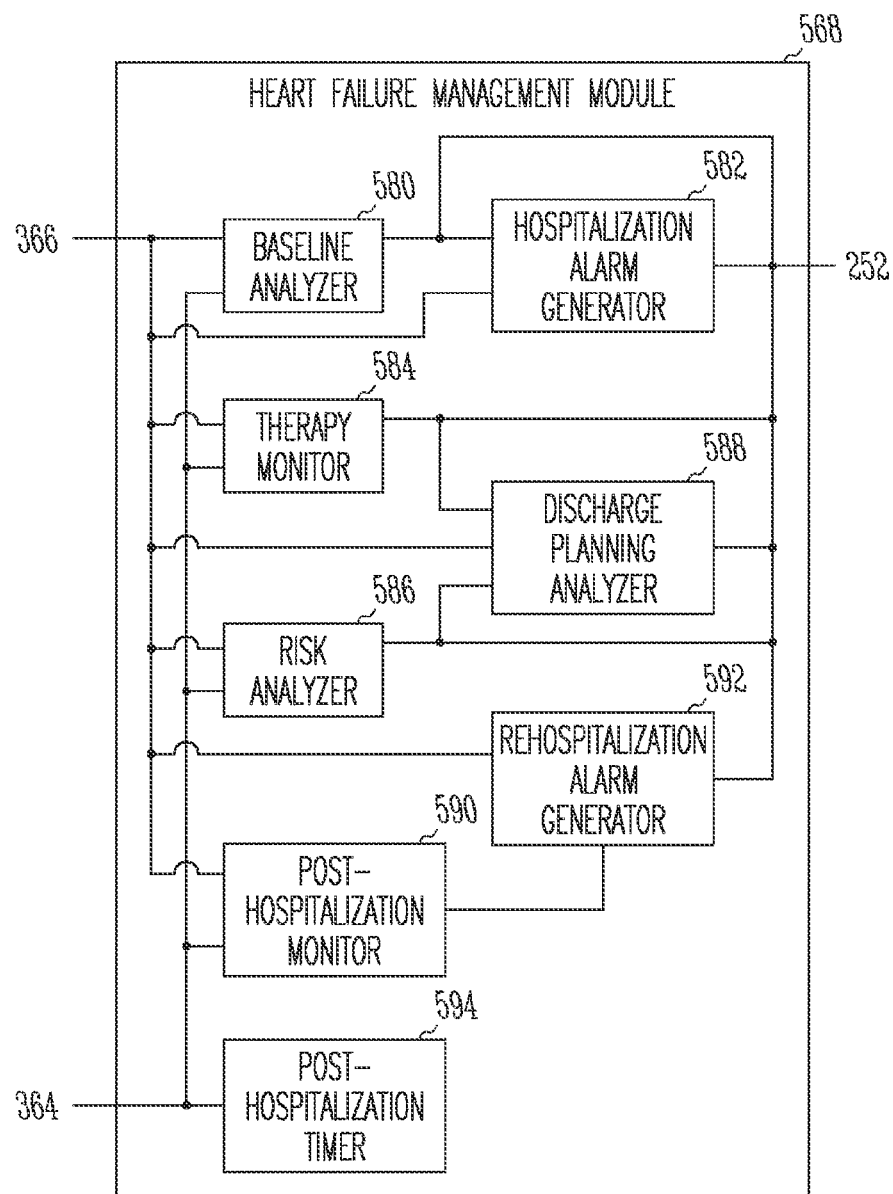
FIG. 5 is a block diagram illustrating an embodiment of a heart failure management module of the heart failure analyzer.

FIG. 5 is a block diagram illustrating an embodiment of a heart failure management module 568, which represents an embodiment of heart failure management module 368. In the illustrated embodiment, heart failure management module 568 includes a baseline analyzer 580, a hospitalization alarm generator 582, a therapy monitor 584, a risk analyzer 586, a discharge planning analyzer 588, a post-hospitalization monitor 590, a rehospitalization alarm generator 592, and a post-hospitalization timer 594.

Baseline analyzer 580 is activated during the non-hospitalization mode and produces one or more baseline values of the one or more parameters produced by diagnostic data processor 366 when the patient is clinically stable. Heart failure is generally characterized by clinically stable periods punctuated by episodes of decompensation and hospitalization. The one or more baseline values of the one or more parameters are produced using the sensor data acquired when decompensation has not been detected for a specified period of time, such as 30 days.

Hospitalization alarm generator 582 produces a hospitalization alarm signal when the one or more parameters indicate a need for hospitalization during the non-hospitalization mode. In various embodiments, the hospitalization alarm signal is produced as a tone audible to the patient and/or transmitted to external system 225 for notifying the patient and/or the physician or other caregiver using presentation device 252. In one embodiment, hospitalization alarm generator 582 produces the hospitalization alarm signal by comparing at least one of the one or more parameters to a corresponding hospitalization threshold value. In another embodiment, hospitalization alarm generator 582 produces the hospitalization alarm signal by comparing a time derivative (slope) of at least one of the one or more parameters to a corresponding hospitalization threshold derivative value. In one embodiment, mode switch 364 switches the operational mode of heart failure analyzer 360 from the non-hospitalization mode to the hospitalization mode in response to the hospitalization alarm signal.

Therapy monitor 584 is activated during the hospitalization mode and analyzes efficacy of therapy using one or more parameters produced by diagnostic data processor 366 and one or more corresponding expected values of the one or more parameters associated with the one or more therapies applied. The one or more therapies are adjusted if the one or more parameters substantially deviate from the one or more expected values.

Risk analyzer 586 is activated during the hospitalization mode and produces a risk class parameter. The risk class parameter classifies a level of risk for rehospitalization. In one embodiment, the level of risk for rehospitalization is a probability of rehospitalization within a specified period of time, and risk analyzer 586 calculates this probability using an empirically established mathematical formula using the one or more parameters produced by diagnostic data processor 366. In one embodiment, risk analyzer 586 produces the class parameter by comparing at least a risk parameter selected from the one or more parameters produced by diagnostic data processor 366 to one or more risk threshold values associated with the risk parameter. In one embodiment, the risk threshold value is a function of the baseline value of the risk parameter. In another embodiment, risk analyzer 586 produces the risk class parameter by comparing a time derivative (slope) of at least one of the one or more parameters to one or more risk threshold derivative values associated with the risk parameter.

Discharge planning analyzer 588 produces a discharge recommendation signal using the risk class parameter during the hospitalization mode. In one embodiment, discharge planning analyzer 588 produces the discharge recommendation signal when the risk class parameter falls below a predetermined or programmed threshold. In one embodiment, mode switch 364 switches the operational mode of heart failure analyzer 360 from the hospitalization mode to the post hospitalization mode in response to the discharge recommendation signal.

Post-hospitalization monitor 590 is activated during the post-hospitalization mode. Post-hospitalization monitor 590 monitors the one or more parameters produced by diagnostic data processor 366 and produces signals indicative of need for medical intervention using the one or more parameters and predetermined and/or programmed criteria associated with the one or more parameters. The intervention may include adjustments of one or more factors affecting conditions associated with heart failure, such as therapy, diet, and daily activities. The adjustments of therapy include, for example, starting a therapy, stopping a therapy, and adjustment of therapy parameters such as drug dosage and pacing parameters. In one embodiment, the patient is monitored more closely in the post-hospitalization mode than in the non-hospitalization mode because the known elevated risk of hospitalization during the period of time (such as 180 days) following the hospitalization. This requires, for example, monitoring of more parameters representing physiological signals sensed by more sensors and analysis of more features extracted from the one or more parameters.

Rehospitalization alarm generator 592 produces a rehospitalization alarm signal when the one or more parameters produced by diagnostic data processor 366 indicate a need for rehospitalization during the post-hospitalization mode. In one embodiment, rehospitalization alarm generator 592 produces the rehospitalization alarm signal by comparing at least one of the one or more parameters to a corresponding rehospitalization threshold value. In another embodiment, rehospitalization alarm generator 592 produces the rehospitalization alarm signal by comparing a time derivative of at least one of the one or more parameters to a corresponding rehospitalization threshold derivative value. In one embodiment, mode switch 364 switches the operational mode of heart failure analyzer 360 from the post-hospitalization mode to the hospitalization mode in response to the rehospitalization alarm signal.

Post-hospitalization tinier 594 times a post-hospitalization period that starts with the post-hospitalization mode. In one embodiment, the post-hospitalization period is a predetermined period. In another embodiment, the post-hospitalization period is programmable, such as using user input device 250. In one embodiment, mode switch 364 switches the operational mode of heart failure analyzer 360 from the post-hospitalization mode to the non-hospitalization mode in response to the expiration of the post-hospitalization period.

Figure 6:
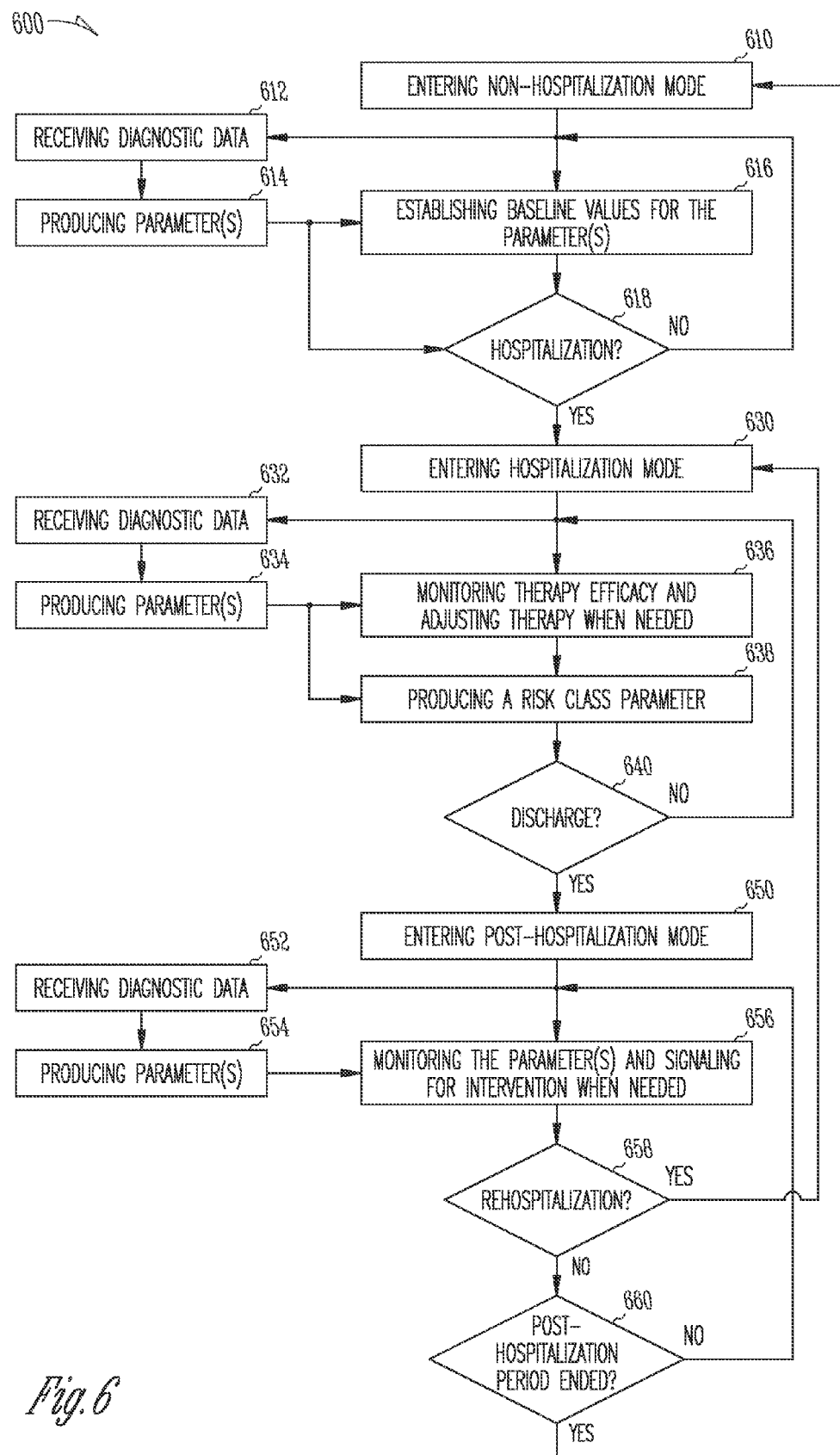
FIG. 6 is a flow chart illustrating a method for managing hospitalization of a heart failure patient.

FIG. 6 is a flow chart illustrating a method 600 for managing hospitalization of a heart failure patient using a hospitalization management system such as hospitalization management system 100. In the illustrated embodiment, the hospitalization management system has a plurality of operational modes including a non-hospitalization mode, a hospitalization mode, and a post-hospitalization mode, and method 600 is applied to operate this hospitalization management system.

At 610, the hospitalization management system enters the non-hospitalization mode. In one embodiment, the hospitalization management system enters each of its operational modes in response to a mode-change command received from a user. In another embodiment, the hospitalization management system enters each of its operational modes in response to a mode-change command produced automatically using patient information including at least a physiological signal sensed from the patient. The hospitalization management system selects a heart failure management algorithm upon entering each of its operational modes and executes that algorithm during the operational mode. During the non-hospitalization mode, the hospitalization management system executes a baseline algorithm.

At 612, diagnostic data indicative of one or more conditions associated with heart failure are received. The diagnostic data include sensor data representative of one or more physiological signals sensed by one or more implantable sensors being part of or communicatively coupled to an implantable medical device of the hospitalization management system. In one embodiment, diagnostic data further include external data representative of patient information stored an external system communicatively coupled to the implantable medical device. In one embodiment, the diagnostic data received during each operational mode include input data required to execute the heart failure management algorithm selected for that operational mode.

At 614, one or more parameters are produced using the diagnostic data. In one embodiment, the selected heart failure management algorithm determines which one or more parameters are produced during each operational mode.

At 616, one or more baseline values for the one or more parameters are established. In one embodiment, a baseline value for each of the one or more parameters is produced using baseline data including sensor data representative of the one or more sensor signals sensed by the one or more implantable sensors within a clinically stable period (when decompensation is not detected) during the non-hospitalization mode.

At 618, whether the patient needs hospitalization is determined. In one embodiment, whether the patient needs hospitalization is determined by comparing at least one of the one or more parameters to a corresponding hospitalization threshold value. In another embodiment, whether the patient needs hospitalization is determined by comparing a time derivative (slope) of at least one of the one or more parameters to a corresponding hospitalization threshold derivative value. In one embodiment, in response to each determination that the patient needs hospitalization, a hospitalization alarm signal is produced.

At 630, the hospitalization management system enters to hospitalization mode after the determination that the patient needs hospitalization is made at 618. If the patient does not need hospitalization as determined at 618, the hospitalization management system remains in the non-hospitalization mode. In one embodiment, the operational mode is switched from the non-hospitalization mode to the hospitalization mode in response to the determination that the patient needs hospitalization (such as in response to the hospitalization alarm signal). In another embodiment, the operational mode is switched from the non-hospitalization mode to the hospitalization mode in response to the mode-change command entered by a physician or other caregiver upon the patient's admission into a hospital. During the hospitalization mode, the hospitalization management system executes a hospitalization algorithm.

At 632, the diagnostic data are received according to the requirement for executing the hospitalization algorithm. At 634, the one or more parameters are produced using the diagnostic data according to the hospitalization algorithm. In various embodiments, the diagnostic data received and the one or more parameters produced during different operational modes may be substantially identical or substantially different, depending on the need for patient monitoring and availability of types of data. In one embodiment, a trend indicative of progression of heart failure is produced using at least one of the one or more parameters. The trend indicates acute worsening of heart failure. In one embodiment, the trend is presented to the physician or other caregiver using a display screen and/or a printer. In one embodiment, the trend is the trend of a parameter being a function of the sensor data and the external data.

At 636, therapy efficacy is monitored, and therapy is adjusted when needed in response to the outcome of the monitoring. The efficacy of therapy administrated during the hospitalization mode is analyzed by comparing the one or more parameters to the corresponding expected values of the one or more parameters. The expected values represent the predicted response of the patient to the therapy. In one embodiment, the therapy delivered includes one or more of an anti-bradycardia pacing therapy, an anti-tachycardia pacing therapy, a defibrillation therapy, a cardiac resynchronization therapy, and a neurostimulation therapy.

At 638, a risk class parameter is produced. The risk class parameter classifies a level of risk for rehospitalization. In one embodiment, the risk class parameter represents the probability of rehospitalization within a specified period. In one embodiment, the risk class parameter is produced by comparing at least one of the one or more parameters to one or more risk threshold values associated with the risk parameter. In another embodiment, the risk class parameter is produced by comparing a time derivative (slope) of at least a risk parameter of the one or more parameters with one or more risk threshold derivative values associated with the risk parameter.

At 640, whether the patient is ready to be discharged from the hospital is determined using the risk class parameter. In one embodiment, in response to a determination that the patient is ready to be discharged, a discharge recommendation signal is produced and presented to the physician or other caregiver.

At 650, the hospitalization management system enters a post-hospitalization mode after the determination that the patient is ready to be discharged at 640. If the patient is not ready to be discharged as determined at 640, the hospitalization management system remains in the hospitalization mode. In one embodiment, the operational mode is switched from the hospitalization mode to the post hospitalization mode in response to the determination that the patient is ready to be discharged (such as in response to the discharge recommendation signal). In another embodiment, the operational mode is switched from the non-hospitalization mode to the hospitalization mode in response to the mode-change command entered by the physician or other caregiver before the patient leaves the hospital. During the post-hospitalization mode, the hospitalization management system executes a post-hospitalization algorithm.

At 652, the diagnostic data are received according to the requirement for executing the post-hospitalization algorithm. At 654, the one or more parameters are produced using the diagnostic data according to the post-hospitalization algorithm.

At 656, the one or more parameters are monitored, and a need for intervention is signaled, when needed, in response to the outcome of the monitoring. Signals indicative of need for intervention are produced during the post-hospitalization mode when the one or more parameters indicate such need according to predetermined and/or programmed criteria. Examples of such intervention include adjustments of one or more factors affecting conditions associated with heart failure, such as therapy parameters, diet, and daily activities.

At 658, whether the patient needs rehospitalization is determined. In one embodiment, whether the patient needs rehospitalization is determined by comparing at least one of the one or more parameters to a corresponding rehospitalization threshold value. In another embodiment, whether the patient needs rehospitalization is determined by comparing a time derivative of at least one of the one or more parameters to a corresponding rehospitalization threshold derivative value. In one embodiment, a rehospitalization alarm signal is produced when the one or more parameters indicate a need for rehospitalization.

In response to a determination that the patients needs rehospitalization at 658, the patient is to be rehospitalized, and the operational mode of the hospitalization management system reenters the hospitalization mode at 630. In one embodiment, the operational mode is switched from the post-hospitalization mode to the hospitalization mode in response to the rehospitalization alarm signal. In another embodiment, the operational mode is switched from the non-hospitalization mode to the hospitalization mode in response to the mode-change command entered by the physician or other caregiver upon the patient's readmission into the hospital.

A post-hospitalization period is started when the hospitalization management system enters the post-hospitalization mode and is timed during the post-hospitalization mode. At 660, if the post-hospitalization period has expired, the operational mode is switched from the post-hospitalization mode to the non-hospitalization mode.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for managing a heart failure patient, the system comprising:
   a sensor processing circuit configured to receive one or more physiological signals and produce sensor data representative of the one or more physiological signals; and
   a heart failure analyzer circuit coupled to the sensor processing circuit, the heart failure analyzer configured to operate in a post-hospitalization mode including to:
      receive diagnostic data including information about the sensor data, the diagnostic data indicative of one or more conditions associated with heart failure decompensation, wherein the diagnostic data includes post-hospitalization respiration data associated with the patient; and
      produce a risk class parameter classifying a level of risk for rehospitalization within a specified period using the diagnostic data.

2. The system of claim 1, wherein the sensor processing circuit is configured to include or to be coupled to an impedance sensor configured to sense a thoracic impedance, and wherein the sensor processing circuit is configured to determine the respiration data using information about the thoracic impedance.

3. The system of claim 2, wherein the sensor processing circuit is configured to determine the respiration data including a respiration characteristic comprising a respiration rate.

4. The system of claim 1, wherein the heart failure analyzer is configured to operate in the post-hospitalization discharge mode upon being triggered by heart failure analyzer circuit determining that the sensor data has met at least one specified criterion.

5. The system of claim 1, wherein the heart failure analyzer is configured to operate in the post-hospitalization discharge mode upon being triggered by a user command being received after a decision to discharge the patient from a hospitalization.

6. The system of claim 1, wherein the heart failure analyzer circuit includes at least one specified re-hospitalization criterion and at least one specified hospitalization criterion, wherein the at least one specified re-hospitalization criterion is easier to meet than the at least one specified hospitalization criterion.

7. The system of claim 1, wherein the heart failure analyzer is configured to include respiration data obtained outside of the post-hospitalization mode in the diagnostic data used to produce the risk class parameter classifying the level of risk for rehospitalization.

8. The system of claim 7, wherein the heart failure analyzer is configured to include respiration data obtained in a hospitalization mode in the diagnostic data used to produce the risk class parameter classifying the level of risk for rehospitalization.

9. The system of claim 8, wherein the heart failure analyzer is configured to include respiration data obtained in a non-hospitalization mode in the diagnostic data used to produce the risk class parameter classifying the level of risk for rehospitalization.

10. The system of claim 1, comprising an implantable medical device including the sensor processing circuit, and a remotely-accessible external patient management system including or coupled to at least a portion of the heart failure analyzer circuit to permit a caregiver to monitor the patient from a remote location.

11. The system of claim 6, wherein the heart failure analyzer circuit is configured to receive the patient's medical history information including patient demographics and history of cardiac and produce the one or more parameters indicative of heart failure decompensation using the diagnostic data including the sensor data and the medical history information.

12. A system for managing a patient, the system comprising:

a heart failure analyzer circuit configured to operate in a post-hospitalization mode including to:
    receive diagnostic data including information about patient physiological sensor data, the diagnostic data indicative of one or more conditions associated with heart failure decompensation, wherein the diagnostic data includes post-hospitalization respiration data associated with the patient; and
    classify a level of risk for rehospitalization using the diagnostic data including using a respiration characteristic comprising a respiration rate.

13. The system of claim 12, wherein the heart failure analyzer is configured to operate in the post-hospitalization discharge mode:
    upon being triggered by heart failure analyzer circuit determining that the sensor data has met at least one specified criterion; and
    upon being triggered by a user command being received after a decision to discharge the patient from a hospitalization.

14. The system of claim 12, wherein the heart failure analyzer circuit includes at least one specified re-hospitalization criterion and at least one specified hospitalization criterion, wherein the at least one specified re-hospitalization criterion is easier to meet than the at least one specified hospitalization criterion.

15. The system of claim 12, wherein the heart failure analyzer is configured to:
    use respiration data obtained in a hospitalization mode in the diagnostic data used to classify the level of risk for rehospitalization; and
    use respiration data obtained in a non-hospitalization mode in the diagnostic data used to classify the level of risk for rehospitalization.

16. The system of claim 12, comprising an implantable medical device including:
    a sensor processing circuit configured to receive one or more physiological signals and produce the sensor data as representative of the one or more physiological signals; and
    a remotely-accessible external patient management system including or coupled to at least a portion of the heart failure analyzer circuit to permit a caregiver to monitor the patient from a remote location.

17. The system of claim 12, wherein the heart failure analyzer circuit is configured to produce one or more parameters indicative of heart failure decompensation using the diagnostic data, and produce a trend indicative of progression of heart failure using at least one parameter of the one or more parameters.

18. The system of claim 17, further comprising a presentation device configured to present the trend.

19. A system for managing a heart failure patient, the system comprising an implantable medical device comprising:
    a sensor processing circuit configured to receive one or more physiological signals and produce sensor data representative of the one or more physiological signals; and
    a heart failure analyzer circuit coupled to the sensor processing circuit, the heart failure analyzer configured to operate in a post-hospitalization mode including to:
        receive diagnostic data including information about the sensor data, the diagnostic data indicative of one or more conditions associated with heart failure decompensation, wherein the diagnostic data includes post-hospitalization respiration data associated with the patient; and
        classify a level of risk for rehospitalization within a specified period using the diagnostic data including respiration rate determined from thoracic impedance.

20. The system of claim 19, wherein the heart failure analyzer circuit includes at least one specified re-hospitalization criterion and at least one specified hospitalization criterion, wherein the at least one specified re-hospitalization criterion is easier to meet than the at least one specified hospitalization criterion.

* * * * *